United States Patent
Digne et al.

(10) Patent No.: US 10,473,391 B2
(45) Date of Patent: Nov. 12, 2019

(54) PROCESS FOR HEATING THE COLUMN FOR DISTILLATION OF THE C3 FRACTION FROM AN FCC UNIT BY MEANS OF A CIRCUIT OF WATER HEATED BY STREAMS BELONGING TO UNITS PLACED UPSTREAM AND/OR DOWNSTREAM OF THE FCC UNIT

(71) Applicant: IFP ENERGIES NOUVELLES, Rueil-Malmaison (FR)

(72) Inventors: Romina Digne, Lyons (FR); Heloise Dreux, Lyons (FR); Frederic Feugnet, Lyons (FR); Nicolas Lambert, Issy-les-Moulineaux (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 839 days.

(21) Appl. No.: 14/902,065

(22) PCT Filed: Jun. 6, 2014

(86) PCT No.: PCT/FR2014/051359
§ 371 (c)(1),
(2) Date: Dec. 30, 2015

(87) PCT Pub. No.: WO2015/001214
PCT Pub. Date: Jan. 8, 2015

(65) Prior Publication Data
US 2016/0348963 A1    Dec. 1, 2016

(30) Foreign Application Priority Data
Jul. 1, 2013    (FR) .................................... 13 56393

(51) Int. Cl.
*F25J 3/02*    (2006.01)
*C10G 69/04*    (2006.01)
(Continued)

(52) U.S. Cl.
CPC ............ *F25J 3/0214* (2013.01); *B01D 3/007* (2013.01); *B01D 3/143* (2013.01); *B01D 3/322* (2013.01);
(Continued)

(58) Field of Classification Search
CPC ........ C10G 7/12; C10G 11/00; C10G 11/185; C10G 45/72; C10G 69/04; B01D 3/007
See application file for complete search history.

(56) References Cited

U.S. PATENT DOCUMENTS

| 4,411,676 A | 10/1983 | Tedder |
| 2009/0203951 A1 | 8/2009 | Kurukchi et al. |

(Continued)

FOREIGN PATENT DOCUMENTS

EP    2088184 A1    8/2009

OTHER PUBLICATIONS

International Search Report and Search Opinion from PCT/FR2014/051359 dated Jul. 28, 2014.

*Primary Examiner* — Tareq Alosh
(74) *Attorney, Agent, or Firm* — Millen White Zelano & Branigan, PC

(57) ABSTRACT

The present invention describes a process for heating the reboiler of the propane/propylene separation column situated downstream of an FCC unit and fed with the C3 cut from said FCC unit, a process consisting of heating the water in a hot water circuit by means of one or more process fluids originating from units placed upstream and/or downstream of the FCC unit and called hot fluids, one of these fluids being constituted by the overhead vapours from the fractionation column connected to the mild hydrocracking unit.

11 Claims, 2 Drawing Sheets

(51) Int. Cl.
*B01D 3/32* (2006.01)
*C07C 7/04* (2006.01)
*B01D 3/00* (2006.01)
*B01D 3/14* (2006.01)
*C10G 45/72* (2006.01)
*C10G 7/12* (2006.01)
*C10G 11/18* (2006.01)

(52) U.S. Cl.
CPC ................ *C07C 7/04* (2013.01); *C10G 7/12* (2013.01); *C10G 11/185* (2013.01); *C10G 45/72* (2013.01); *C10G 69/04* (2013.01); *C10G 2300/4006* (2013.01)

(56) References Cited

U.S. PATENT DOCUMENTS

| | | | |
|---|---|---|---|
| 2014/0174985 A1* | 6/2014 | Dreux | C10G 47/36 208/113 |
| 2014/0353211 A1* | 12/2014 | Digne | C10G 67/02 208/97 |

* cited by examiner

PROCESS FOR HEATING THE COLUMN FOR DISTILLATION OF THE C3 FRACTION FROM AN FCC UNIT BY MEANS OF A CIRCUIT OF WATER HEATED BY STREAMS BELONGING TO UNITS PLACED UPSTREAM AND/OR DOWNSTREAM OF THE FCC UNIT

FIELD OF THE INVENTION

The invention relates to the field of the separation by fractionation of propane and propylene originating from a fluid catalytic cracking (FCC) unit. C3 cuts originating from a delayed coking unit, visbreaker or any other process aimed at producing propylene, can also be added to the C3 cut originating from the FCC in order to separate the propane from the propylene present in these cuts. The purity of the propylene obtained after fractionation is generally that corresponding to polymer grade (>99.5% by weight).

Propane and propylene have very close boiling points, separation by fractionation is therefore very costly in terms of investment and utilities, and there is therefore a great need to reduce this energy expenditure.

EXAMINATION OF THE PRIOR ART

The separation of propane and propylene by fractionation can typically be carried out:
  either at high pressure (approximately 20-25 bar) with condensation of the overhead vapours by cooling water
  or at low pressure (approximately 10-15 bar and less) with recompression of the overhead vapours in order to reboil the column (system with heat pump)

The separation of propane and propylene by fractionation with a heat pump is very often more advantageous economically, but its operation is more complex. Certain refiners therefore prefer to use "high-pressure" separation with condensation of the overhead vapours by means of cooling water.

In the case of a "high-pressure" fractionation, the temperature at the bottom of the column is approximately 63° C. Reboiling, i.e. supplying the calories necessary to reach the temperature at the bottom of the column, can be carried out by means of:
  process fluids from the FCC unit,
  low-pressure steam,
  hot water circulating in a closed loop (hot water circuit).

Generally, the reboiling of the propane/propylene fractionation column is not carried out entirely by heat exchange with process fluids from the FCC unit for the following reasons:
  the energy requirements are very high,
  the process fluids to be cooled, the temperature of which is greater than 200° C., are used to heat flows that are hotter than the bottom of the propane/propylene fractionation column or to produce average- and high-pressure steam, in order to have more effective heat integration.

The process fluids used for reboiling the propane/propylene fractionation column are generally gasoline originating from the debutanizer and/or the upper circulating reflux from the main fractionation column, fluids having moderate temperatures.

Reboiling, at least partially, of the propane/propylene fractionation column with low-pressure steam or hot water circulating in a closed loop is therefore generally necessary.

The principle of the hot water circuit is as follows:
  water at approximately 65° C. is heated to a temperature of approximately 91° C. by means of process fluids from the FCC unit in a variant configuration depending on the power necessary for reboiling the propane/propylene fractionation column as well as on the availability of the following flows:
    overhead vapours from the main fractionation column of the FCC unit,
    vapours originating from the different stages of the cracked gas compressor (wet gas compressor),
    gasoline originating from the debutanizer of the FCC unit,
    upper circulating reflux from the main fractionation column of the FCC unit,
    overhead vapours from the gasoline separation column (naphtha splitter), if there is one, of the FCC unit,
    LCO originating from the main fractionation column of the FCC unit.
  water at approximately 91° C., will reboil the propane/propylene fractionation column. Having reboiled the column, the temperature of the water is again equal to approximately 65° C.
  the water at approximately 65° C. will again be heated to approximately 91° C. by means of process fluids from the FCC unit listed previously.

The hot water circuit is a closed-loop circuit. Pumps are necessary for the circulation of the hot water in said circuit, as well as a water make-up tank in order to compensate for any losses of water and an air cooler in order to dissipate the heat not used during the transitional phases (start-up, shut-down, etc.).

The reboiling of the propane/propylene separation column is typically carried out at two levels in order to benefit from the best possible thermal approaches:
  with a reboiler at the bottom of the column using the hot water at approximately 91° C. and returning it at approximately 75° C.,
  with an intermediate reboiler using the hot water at approximately 75° C. and returning it at approximately 65° C.

The intermediate reboiler corresponds to approximately 40% of the total power of the two reboilers. The intermediate reboiler makes it possible to have a better thermal approach using the two reboilers together.

The temperature at the top of the main fractionation column is generally minimized in order to maximize the quality of the products originating from the fractionation and the heat recovery while avoiding the condensation of water in the fractionation column for reasons of corrosion. The temperature at the top of the fractionation column generally corresponds to the water dew point+25° C.

The margin of 25° C. makes it possible to avoid corrosion in the upper part of the column. Therefore the temperature at the top of the fractionation column is generally comprised between 100° C. and 120° C. When a hot water circuit is installed within the FCC unit, an increase in the temperature at the top of the fractionation column is often required in order to have a better thermal approach in the exchanger heating the hot water. This practice causes the quality of the fractionation to deteriorate and does not allow enhanced thermal optimization.

Furthermore, when the FCC unit has a high propylene yield, or when the separation of cuts rich in propylene outside the FCC unit is required, the hot water circuit does not make it possible to completely reboil the propane/propylene fractionation column.

A reboiler with low-pressure steam is therefore necessary in order to make up the supply of calories.

BRIEF DESCRIPTION OF THE INVENTION

Figure 1:
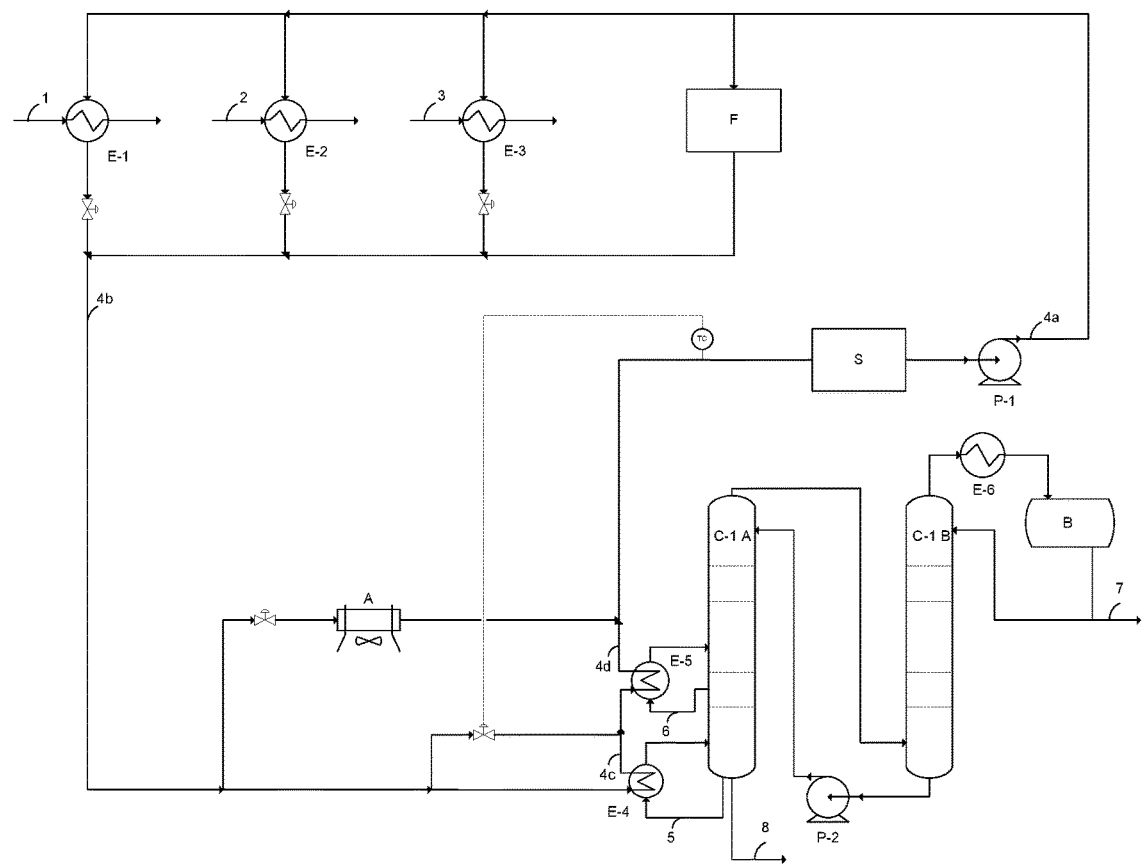
FIG. 1 is a diagram of the hot water loop process according to the present invention showing the possible different hot fluids. The loop itself has as many exchangers as there are new hot fluids utilized.
Figure 2:
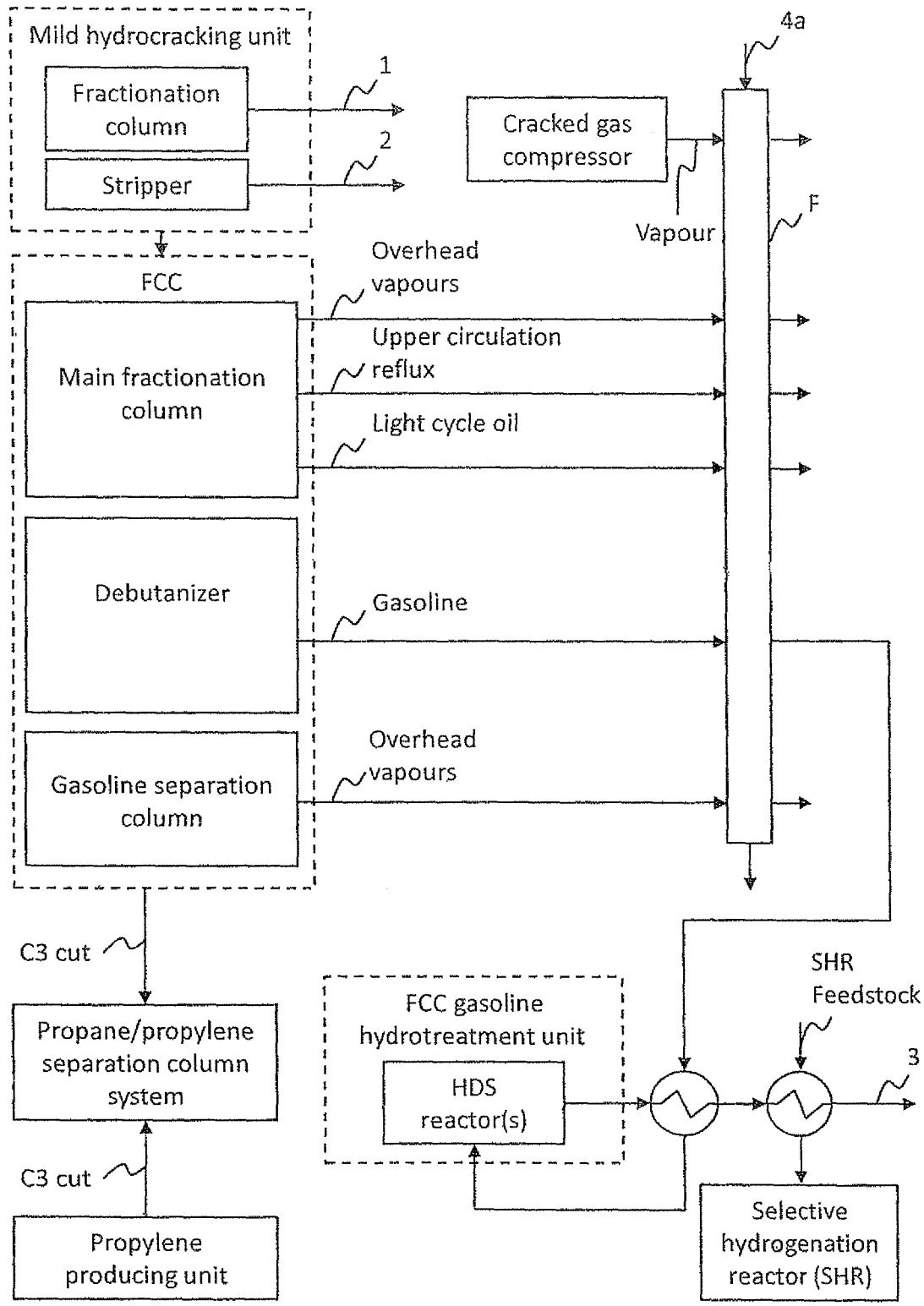
FIG. 2 is a flow chart showing a mild hydrocracking unit, cracked gas processor, FCC unit, an FCC gasoline hydrotreatment unit having HDS reactor(s), a selective hydrogenation (SHU) reactor, a propane/propylene separation column system, and a propylene producing unit, and streams associated therewith, in accordance with the present invention.

The present invention can be defined as a process for heating the reboiler of the propane/propylene separation column system situated downstream of an FCC unit and fed with the C3 cut from said FCC unit. The expression "column system" is used to indicate that the propane/propylene separation can be carried out by means of one or more separation columns arranged in series.

When there is a single column, the reboiler is that of the column considered.

When there are several columns arranged in series, the reboiler is that of the first column in the direction of fluid flow, the top of this first column feeding the bottom of the second column and so on if there are more than two columns.

The process according to the present invention consists of heating the water in a hot water circuit by means of one or more process fluids originating from units placed upstream and/or downstream of the FCC unit and called "hot" fluids, said hot fluids being chosen, alone or in combination, from the following fluids:
- overhead vapours from the fractionation column of the mild hydrocracking unit upstream of the FCC unit,
- overhead vapours from the stripper of the mild hydrocracking unit upstream of the FCC unit,
- effluent from the hydrodesulphurization (HDS) reactor(s) of the FCC gasoline hydrotreatment unit, if there is one downstream of the FCC unit, after heat exchanges with the feedstock of the HDS reactor(s) and with the feedstock of the selective hydrogenation (SHU) reactor.

The heating of the water in the hot water circuit according to the present invention can optionally be completed by the use of at least one of the following fluids in addition to one of the hot fluids:
- overhead vapours from the main fractionation column of the FCC unit,
- vapours originating from the different stages of the cracked gas compressor,
- gasoline originating from the debutanizer of the FCC unit,
- upper circulating reflux from the main fractionation column of the FCC unit,
- overhead vapours from the gasoline separation column of the FCC unit,
- LCO (light cycle oil) originating from the main fractionation column of the FCC unit.

The process of heating the reboiler of the propane/propylene separation column system situated downstream of an FCC unit according to the present invention, is fed with the C3 cut from said FCC unit to which can be added, according to a variant, a C3 cut originating from another process aimed at producing propylene. By way of example of another process (meaning distinct from the FCC), the process of converting olefins to propylene may be mentioned.

The process of heating the reboiler of the propane/propylene separation column (C-1 A) according to the present invention can be defined more precisely when the propane/propylene separation system is constituted by two columns C-1 A and C-1 B connected in series as follows: the liquid at the bottom of the column C-1 B is pumped then sent to the top of the column C-1 A, the overhead vapours of C-1 B are condensed with cooling water then sent into the reflux tank B of the column C-1 B, the propylene (flow 7) is recovered at the top of C-1 B and the propane (flow 8) at the bottom of C-1 A, the two columns (C-1 A and C-1 B) being situated downstream of an FCC unit.

The process according to the invention is defined thus: the water in the hot water circuit is heated from 65° C. (flow 4a) to 91° C. (flow 4b) via exchangers which are in parallel (E-1, E-2, E-3 etc.) by at least one of the following novel process flows:
- overhead vapours from the fractionation column of the mild hydrocracking unit upstream of the FCC unit (flow 1) by means of the exchanger E-1,
- overhead vapours from the stripper of the mild hydrocracking unit upstream of the FCC unit (flow 2) by means of the exchanger E-2,
- effluent from the HDS reactor(s) of the FCC gasoline hydrotreatment unit (flow 3) by means of the exchanger E-3 if there is an FCC gasoline hydrotreatment unit downstream of the FCC unit. The flow 3 having been used beforehand in order to heat the feedstock of the HDS reactor(s), and the feedstock of the selective hydrogenation (SHU) reactor, the reboiling of the propane/propylene separation column (C-1 A) being carried out at two levels:
- with a reboiler at the bottom of the column (E-4), heating the flow 5 by means of the hot water at 91° C. (flow 4b) and returning the water at approximately 75° C. (flow 4c),
- with an intermediate reboiler (E-5), heating the flow 6 by means of the hot water at approximately 75° C. (flow 4c) and returning the water at 65° C. (flow 4d).

DETAILED DESCRIPTION OF THE INVENTION

The present invention falls within the context of supplying calories to the reboiler of the propane/propylene fractionation column located downstream of the fluid catalytic cracking (abbreviation: FCC) unit.

The invention consists of heating the water in a hot water circuit with process fluids from units placed upstream and/or downstream of the FCC unit, optionally in addition to the usual process fluids from the FCC unit already described in the prior art.

The hot water circuit making possible the supply of calories to the reboiler of the propane/propylene fractionation column is described in FIG. 1 according to the invention.

FIG. 1 shows the "high-pressure" propane/propylene fractionation column, generally constituted by 2 columns (C-1 A and C-1 B) given the high number of trays (between 200 and 300) and the usual height restrictions associated with the siting of industrial columns (approximately 100 metres maximum).

The liquid at the bottom of the column C-1 B is pumped then sent to the top of the column C-1 A.

The overhead vapours of C-1 B are condensed with cooling water then sent into the reflux drum B.

The propylene (flow 7) is recovered at the top of C-1 B and the propane (flow 8) at the bottom of C-1 A.

In the process according to the invention, the water in the hot water circuit is heated from 65° C. (flow 4a) to 91° C. (flow 4b) via exchangers which are in parallel (E-1, E-2, E-3 etc.) by the following new process flows:
- overhead vapours from the fractionation column of the mild hydrocracking unit upstream of the FCC unit (flow 1) by means of the exchanger E-1,
- overhead vapours from the stripper of the mild hydrocracking unit upstream of the FCC unit (flow 2) by means of the exchanger E-2,
- effluent from the HDS reactor(s) of the FCC gasoline hydrotreatment unit (flow 3) by means of the exchanger E-3, if there is an FCC gasoline hydrotreatment unit downstream of the FCC unit. The flow 3 having been used beforehand for heating the feedstock of the HDS reactor(s), and the feedstock of the selective hydrogenation (SHU) reactor.

The fluids in the hot water circuit can also be made up with the process fluids from the FCC unit described in the prior art via the operation F.

The reboiling of the propane/propylene separation column (C-1 A) is carried out at two levels:
- with a reboiler at the bottom of the column (E-4), heating the flow 5 by means of the hot water at 91° C. (flow 4b), and returning the water at approximately 75° C. (flow 4c),
- with an intermediate reboiler (E-5), heating the flow 6 by means of the hot water at approximately 75° C. (flow 4c) and returning the water at 65° C. (flow 4d).

In the process according to the invention, it is possible to further heat hot water and thus obtain a reboiling of the propane/propylene fractionation column without consuming low-pressure steam.

Furthermore, the process fluids from the units upstream and downstream of the FCC unit, making it possible to heat the water, have a generally higher temperature than the process fluids from the FCC unit (Table 1 below).

As a result, the difference in temperature between the hot and cold flows in the exchangers (E-1, E-2, E-3 etc.) heating the hot water is greater, which reduces the cost of said exchangers, and therefore the cost of the hot water circuit.

TABLE 1

Temperatures of the process fluids capable of heating the water of the hot water circuit

| | Process flow | Temperature (° C.) |
|---|---|---|
| New flow according to the invention | Overhead vapours from the fractionation column (mild hydrocracking unit) | 120 to 140 |
| | Overhead vapours from the stripper (mild hydrocracking unit) | 150 to 180 |
| | Effluent from the HDS reactor(s) (FCC gasoline hydrotreatment unit) | >120 |
| Flow known from the prior art | Overhead vapours from the main fractionation column (FCC unit) | 100 to 120 |
| | Gasoline originating from the debutanizer (FCC unit) | 120 to 180 |
| | Upper circulating reflux of the main fractionation column (FCC unit) | 120 to 140 |
| | Overhead vapours from the gasoline separation column (FCC unit) | 110 to 130 |

TABLE 1-continued

Temperatures of the process fluids capable of heating the water of the hot water circuit

| Process flow | Temperature (° C.) |
|---|---|
| LCO originating from the main fractionation column (FCC unit) | >160 |

All these flows, new or already known from the prior art, are capable of heating the water circulating in the hot water loop used for reboiling the propane/propylene separation column according to a variant configuration depending on the power necessary for reboiling the propane/propylene fractionation column as well as on the availability of the flow.

The process according to the present invention is implemented as soon as use is made either of the overhead vapour from the fractionation column connected to the mild hydrocracking unit, or of the overhead vapour from the stripper connected to the mild hydrocracking unit, or also of the hot effluent from the HDS reactor(s) (when such a unit exists). Any combination of these three flows, used in part or in full, falls within the scope of the present invention.

The flows having a high temperature are preferred in order to minimize the area of the exchangers utilized. However, any combination of fluids (new or forming part of the prior art), as soon as at least one new fluid among the three preceding ones is used in the hot water loop, must be understood as forming part of the present invention.

Example According to the Invention

A mild hydrocracking unit processing 458 t/h of vacuum distillate (79% originating from vacuum fractionation and 21% originating from a coking unit) produces 304 t/h of residue. The reaction section of the mild hydrocracking unit comprises 3 reactors in series and 7 catalytic beds. The average temperature of each bed is 403° C. during the lifetime of the catalyst. The partial hydrogen pressure is 85 bar (abs) and the hourly space velocity (HSV) is 0.31 h$^{-1}$.

The residue of the mild hydrocracking unit is sent into an FCC unit operating under severe conditions and with the addition of ZSM-5 to the catalyst in order to maximize the propylene yield.

The propylene yield of the FCC unit is 9% by weight relative to the feedstock.

The FCC unit comprises a LPG (liquefied petroleum gas) fractionation section constituted by a depropanizer, a deethanizer and a high-pressure propane/propylene fractionation column in order to obtain propylene with a purity of 99.6 mol. %.

A C3 cut originating from a coking unit (13 t/h) is added to the LPG originating from the FCC at the inlet to the LPG fractionation section.

The propane/propylene separation column has a feed of 47 t/h the composition by mass of which is as follows: 66% propylene, 33% propane and less than 1% C4+.

The pressure at the bottom of the propane/propylene fractionation column is 22 bar (abs).

The heating power necessary for reboiling the propane/propylene separation column is 52 MW (MW is the abbreviation of megawatt i.e. 10$^6$ watt).

There is no FCC gasoline hydrotreatment unit downstream of the FCC unit as the sulphur content of the gasoline originating from the FCC unit is less than 10 ppm.

The process fluids from the FCC unit available for heating the water in the hot water circuit are shown in Table 2 below.

The log mean temperature difference (LMTD) is shown for each exchange. The greater the LMTD value, the smaller the exchange surface area will be.

TABLE 2

Flows available for heating the water in the hot water circuit (according to the prior art)

| Available process fluids from the FCC unit | inlet T (° C.) | outlet T (° C.) | Duty (MW) | LMTD (° C.) |
|---|---|---|---|---|
| Overhead vapours from the main fractionation column | 100 | 70 | 20 | 6.8 |
| Gasoline originating from the debutanizer | 158 | 70 | 11 | 23.9 |
| Total | | | 31 | |

Only 31 MW of the 52 MW necessary can be supplied inside the FCC unit.

In this example:
there is no gasoline separation column,
the gasoline at the bottom of the debutanizer first heats the feedstock of the debutanizer then the hot water,
the upper circulating reflux from the main fractionation cannot be used, as it heats the reboiler of the deethanizer,
the LCO cannot be used as it heats the feedstock of the debutanizer.

In total, 21 MW of low-pressure steam is therefore necessary in order to complete the heating of the reboiler of the propane/propylene fractionation column.

Table 3 below shows the process fluids available for heating the water in the hot water circuit according to the invention.

TABLE 3

Flows available for heating the water in the hot water circuit (according to the invention)

| | Available process fluids (unit) | inlet T (° C.) | outlet T (° C.) | Duty (MW) | LMTD (° C.) |
|---|---|---|---|---|---|
| Flow according to the prior art | Overhead vapours from the main fractionation column (FCC unit) | 100 | 70 | 20 | 6.8 |
| | Gasoline originating from the debutanizer (FCC unit) | 158 | 70 | 11 | 23.9 |
| New flow according to the invention | Overhead vapours from the fractionation column (mild hydrocracking unit) | 121 | 88 | 34 | 26.3 |
| | Overhead vapours from the stripper (mild hydrocracking unit) | 150 | 70 | 8 | 21.9 |
| | Total | | | 73 | |

Table 3 shows that the heating power available for heating the water (73 MW) is greater than that required (52 MW). The exchanges with the greatest temperature differences (LMTD) are preferred as they are less costly. In this example, the propane/propylene separation column can be reboiled entirely by means of a hot water circuit comprising the following exchanges for heating the water:
overhead vapours from the fractionation column of the mild hydrocracking unit/hot water (34 MW),
gasoline originating from the debutanizer/hot water (11 MW),
overhead vapours from the stripper of the mild hydrocracking unit/hot water (8 MW).

The hot water no longer needs to be heated by the overhead vapours from the main fractionation column of the FCC unit. This exchange has been dispensed with as it had the smallest temperature difference (LMTD) and therefore the highest "exchange surface/exchanged power" ratio.

The invention claimed is:

1. A process for heating a reboiler of a propane/propylene separation column system which is fed with a C3 cut from a fluid catalytic cracking unit, said process comprising:
heating water in a water circuit heat exchange with one or more process fluids originating from units positioned upstream and/or downstream of said fluid catalytic cracking, and then using the heated water in the water circuit to heat said reboiler of the propane/propylene separation column system, wherein said one or more process fluids are:
an overhead vapor stream from a fractionation column of a mild hydrocracking unit positioned upstream of said fluid catalytic cracking,
an overhead vapor stream from a stripper of a mild hydrocracking unit positioned upstream of said fluid catalytic cracking unit, and/or
effluent from a hydrodesulphurization reactor of a fluid catalytic cracking gasoline hydrotreatment positioned downstream of said fluid catalytic cracking unit, after said effluent undergoes heat exchange with a feedstock of the hydrodesulphurization reactor and with a feedstock of a selective hydrogenation reactor.

2. The process according to claim 1, wherein the water is also heated in the water circuit by at least one fluid selected from the following fluids:
an overhead vapor stream from a main fractionation column of said fluid catalytic cracking unit,
a vapor stream originating from a stage of a cracked gas compressor,
a gasoline stream originating from a debutanizer of said fluid catalytic cracking unit,
an upper circulating reflux from a main fractionation column of said fluid catalytic cracking unit,
an overhead vapor stream from a gasoline separation column of said fluid catalytic cracking unit,
a light cycle oil originating from the main fractionation column of said fluid catalytic cracking unit.

3. The process according to claim 1, wherein said propane/propylene separation column system is also fed with a C3 cut originating from a propylene producing unit.

4. The process according to claim 3, wherein said propylene producing unit is a unit for conversion of olefins to propylene.

5. The process according to claim 1, wherein
said propane/propylene separation column system comprises a first propane/propylene separation column having a top and a bottom, and a second propane/propylene separation column having a top and a bottom,
wherein liquid from the bottom of the second propane/propylene separation column is pumped to the top of the first propane/propylene separation column, overhead vapor from the second propane/propylene separation column is condensed with cooling water and then sent to a reflux drum of the second propane/propylene separation column, propylene is recovered from the top of the second propane/propylene separation column, and propane is recovered from the bottom of the first propane/propylene separation column, wherein the water heated in the water circuit is heated by heat exchange with said one or more process fluids via heat exchangers which are arranged in parallel, wherein the reboiler of the propane/propylene separation column system that is heated by the water circuit is a reboiler at the bottom of the first propane/propylene separation column, and wherein said water circuit is also used to heat an intermediate reboiler of the first propane/propylene separation column.

6. The process according to claim 1, wherein said water in said water circuit is heated by heat exchange with said overhead vapor stream from said fractionation column of said mild hydrocracking unit.

7. The process according to claim 1, wherein said water in said water circuit is heated by heat exchange with said overhead vapor stream from said stripper of said mild hydrocracking unit.

8. The process according to claim 1, wherein said water in said water circuit is heated by heat exchange with said effluent from said hydrodesulphurization reactor of said fluid catalytic cracking gasoline hydrotreatment.

9. The process according to claim 1, wherein said propane/propylene separation column system comprises a plurality of columns arranged in series, and wherein said reboiler that is heated by said water circuit is in the first column in the series of columns.

10. The process according to claim 9, wherein said reboiler is a bottom reboiler in said first column in the series of columns, and wherein said first column in the series of columns also comprises an intermediate reboiler, and said intermediate reboiler is also heated by said water circuit.

11. The process according to claim 10, wherein the water of said water circuit is cooled in said bottom reboiler from 91° C. to 75° C., and the water of said water circuit is cooled in said intermediate reboiler from 75° C. to 65° C.

* * * * *